United States Patent [19]

Tiep

[11] 4,120,300
[45] Oct. 17, 1978

[54] BREATHING APPARATUS

[75] Inventor: Brian L. Tiep, Monrovia, Calif.

[73] Assignee: City of Hope National Medical Center, Duarte, Calif.

[21] Appl. No.: 745,591

[22] Filed: Nov. 29, 1976

[51] Int. Cl.$^2$ ............................................. A61M 16/00
[52] U.S. Cl. .................................. 128/203; 128/145.8; 137/835
[58] Field of Search ............... 128/203, 188, 205, 202, 128/145.8, 145.7, 145.6, 145.5, 142, 142.2, 142.3, 147; 137/835

[56] References Cited

U.S. PATENT DOCUMENTS

| | | | |
|---|---|---|---|
| 2,352,523 | 6/1944 | Emerson | 128/145.8 |
| 3,262,446 | 7/1966 | Stoner | 128/145.7 |
| 3,389,698 | 6/1968 | Kadosch et al. | 128/203 |
| 3,473,529 | 10/1969 | Wallace | 128/145.7 |
| 3,565,564 | 2/1971 | Pavlin et al. | 128/145.5 |
| 3,643,660 | 2/1972 | Hudson et al. | 128/206 |
| 3,687,137 | 8/1972 | Johnson | 128/188 |
| 3,726,274 | 4/1973 | Bird et al. | 128/145.8 |
| 3,973,564 | 8/1976 | Carden | 128/145.8 X |
| 4,030,492 | 6/1977 | Simbruner | 128/145.8 |

Primary Examiner—Henry J. Recla
Attorney, Agent, or Firm—Edward D. O'Brian

[57] ABSTRACT

A breathing apparatus primarily intended to be used in administering oxygen to a patient can be constructed so as to utilize a fluidic control device in such a manner as to conserve oxygen. The control device is connected to a supply of the gas to be administered to the user, to a reservoir type structure for temporarily storing this gas and a respiration structure such as a connected pair of tubes adapted to extend loosely into the nostrils of the user. On inhalation through the respiration structure the control device serves to permit gas flow from both the supply and the reservoir type structure to the respiration structure and to the user while on exhalation by the user the control device is responsive to the pressure exerted by the flow of exhaled gas in order to cause gas flow from the supply to the reservoir type structure.

13 Claims, 2 Drawing Figures

BREATHING APPARATUS

BACKGROUND OF THE INVENTION

The invention set forth in this specification relates to new and improved breathing apparatuses. A breathing apparatus in accordance with this invention is especially constructed for use with and is primarily intended for use in administering oxygen to a patient. It is, however, considered that breathing apparatuses in accordance with this invention can be employed for other purposes such as, for example, in supplying a breathable gas mixture to an individual in a location where the ambient air or gas is not breathable or to an individual engaged in scuba or underwater type activities or to an individual at an elevated altitude.

It is a matter of common knowledge that many different types of breathing apparatuses have been developed and utilized in the past. It is considered that those breathing apparatuses which have been primarily developed for and/or used in administering oxygen to a patient have been relatively undesirable because in effect they tend to "waste" oxygen in the sense that substantially all of the oxygen supplied to a patient through such an apparatus is not effectively delivered to the respiratory tract of the patient.

This is considered to be quite important in connection with the treatment of many patients because of the relative cost of oxygen. It has been recognized that if the oxygen used in treating patients could be more effectively utilized that many individuals would be better able to afford needed oxygen treatment. Common prior apparatuses for oxygen therapy have been constructed so that during a part of the breathing cycle of a patient some oxygen would escape to the ambient air.

It is recognized that various different types of breathing apparatuses known as "rebreathers" have been developed and utilized. In theory such "rebreathers" are advantageous inasmuch as they minimize the escape of breathable gas to the ambient surroundings. Many of such "rebreathers" have been utilized in connection with scuba or underwater type activities. While prior "rebreather" type breathing apparatuses are considered to be reasonably utilitarian in character it is also considered that such apparatuses in general tend to be unnecessarily complex and expensive. It is considered that the utilization of such prior "rebreathing" type apparatuses tends to be limited to a degree by what may be loosely referred to as reliability type problems. In the field of breathing apparatuses for use in oxygen therapy reliability is, of course, quite important. Further, the cost of the apparatus is also significant in making such therapy reasonably available.

SUMMARY OF THE INVENTION

An objective of the present invention is to provide new and improved breathing apparatuses of a type primarily designed for use in administering oxygen to a patient but which are also capable of being utilized for other purposes. A further objective of the invention is to provide breathing apparatuses as indicated which may be easily and conveniently constructed at a comparatively nominal cost and which are of such a character as to be extremely reliable in operation. A still further objective of the invention is to provide breathing apparatuses which are effective in minimizing the oxygen used in treatment of a patient so as to tend to reduce the cost of administering oxygen to a patient.

In accordance with this invention these various objectives are achieved by providing a breathing apparatus having a supply means for supplying a gas capable of being breathed, a reservoir means for temporarily storing the gas, a respiration means for conveying a gas to and from the respiratory tract of a user and a control means responsive to the inhalation and exhalation from and into the respiration means, the control means being connected to the supply, reservoir and respiration means in which the improvement comprises: the control means being a fluidic device responsive to a variation in the gas pressure within the respiration means so as to permit flow from both the supply and reservoir means into the respiration means upon inhalation through the respiration means and so as to cause gas flow from the supply means into the reservoir means upon exhalation into the respiration means.

BRIEF DESCRIPTION OF THE DRAWING

Because of the nature of the invention it is best more fully explained with reference to the accompanying drawing in which.

Figure 1:
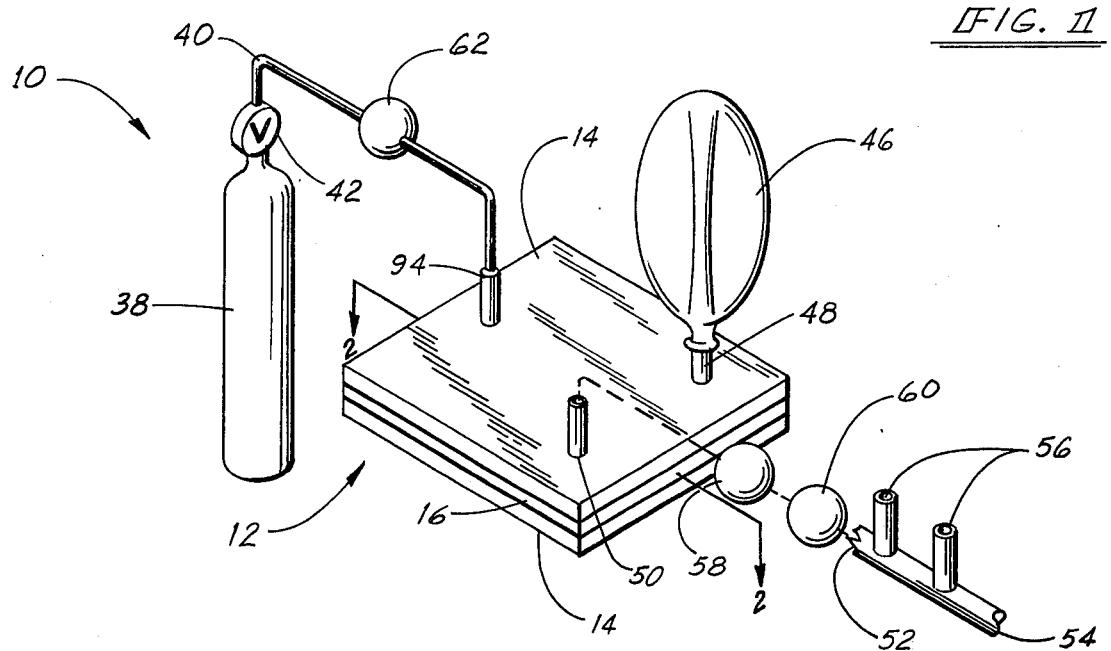
FIG. 1 is a diagrammatic view of a presently preferred form or embodiment of a breathing apparatus of the present invention in which the control means or device used is shown in isometric projection.

The specific apparatus illustrated utilizes the operative principles or features of the invention set forth and defined in the appended claims. It is considered reasonably self-evident that these principles or features can be utilized within a wide variety of differently constructed and/or differently appearing breathing apparatuses through the use or exercise of routine skill in the breathing apparatus and fluidics fields.

DETAILED DESCRIPTION

The breathing apparatus 10 illustrated in the accompanying drawing utilizes as a control means or a control device a small fluidics device 12 which appears essentially as a flat plate-like unit consisting of top and bottom cover plates 14 secured as, for example, by an appropriate adhesive to a center plate 16 which is "cut out" so as to create within the device 12 a series of chambers, ports and passages as hereinafter indicated.

This device 12 includes a supply chamber 18 from which there extends a restricted supply port or nozzle 20 leading into an interaction chamber 22. An output port 24 leads from this interaction chamber 22 into a respiration chamber 26 of an enlarged, elongated character. Another output port 28 leads from the interaction chamber 22 to an output reservoir chamber 30 which is also of an enlarged, elongated character. These output ports 24 and 28 are separated from one another adjacent to the interaction chamber 22 by what may be referred to as a wedge shaped splitter 32. A first feedback passage 34 leads from the respiration chamber 26 into the interaction chamber 22 immediately adjacent the supply port 20. A second feedback passage 36 leads from the reservoir chamber 30 to the interaction chamber 22 adjacent to the supply port 20.

Figure 2:
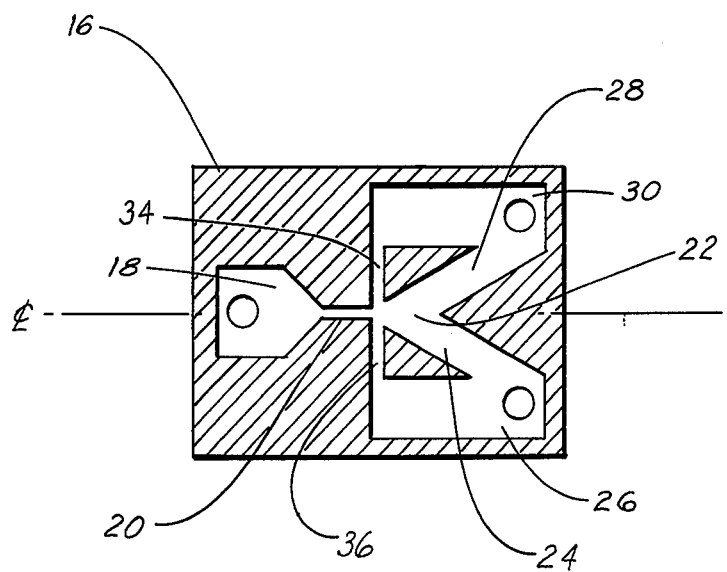
FIG. 2 is a cross-sectional view taken at line 2—2 of FIG. 1 showing the interior of the control means or device employed.

This internal structure within the device 12 is of a bilaterally symmetrical character. The portions of the device 12 on each side of the dotted line C shown in FIG. 2 are bilaterally symmetrical. With this structure the supply port 20 is directed toward the pointed extremity (not separately numbered) of the splitter 32 directed toward the interaction chamber 22. Further, the feedback passages 34 and 36 are small passages located at opposite sides of the supply port 20 where the supply port enters the interaction chamber 22 and are perpendicular to the supply port 20 in the embodiment of the device 12 illustrated.

This entire structure of the device 12 serves as what may be referred to as a bistable fluidic amplifier. This device 12 may also be referred to as a fluidic flip-flop or fluidic flip-flop logic element. It will be realized that various modifications may be made within the internal structure of the device 12 in accordance with known technology in the fluidics field. The invention set forth herein is not primarily concerned with the internal structure of the device 12 but rather with the utilization of a fluidics device of a simple character in connection with and as an integral part of a breathing apparatus 10.

The particular apparatus 10 preferably includes a tank 38 holding pressurized oxygen connected through a line 40 containing an appropriate conventional regulator valve 42 to a conventional inlet port 44 leading into the supply chamber 18. Under appropriate circumstances any known supply means for a gas capable of being breathed may, of course, be substituted for the tank 38.

The apparatus 10 also includes an elastomeric sack 46 connected to the reservoir chamber 30 by means of another port 48 corresponding to the port 44 previously described. In practice any rubber balloon of reasonable quality can be utilized as the sack 46. In effect the sack 46 serves as a variable volume reservoir for use in temporarily storing a gas or gas mixture as the complete apparatus 10 is used. Thus, this sack 46 may be regarded as a species or type of a variable volume gas storage structure or as a species or type of an accumulator. From a consideration of this complete specification it will be realized that a variety of structures may be utilized in place of or in lieu of the sack 46. For example, if the apparatus 10 is to be used for scuba or similar activities it is considered that it will be preferable to enclose the sack 46 in an appropriate protective container (not shown) so as to isolate it from the ambient water pressure.

The apparatus 10 further includes another port 50 connected to the respiration chamber 26 which is used to attach an elongated tube 52 to the device 12. This tube 52 has an enclosed end 54 provided with two tubular outlets 56 of such a dimension as to be capable of fitting loosely within the nostrils of a user of the apparatus 10. This entire tube 52 may be regarded as a respiration structure or respiration means since it is utilized in connection with gas flow as hereinafter indicated. It will, of course, be realized that a wide variety of different substantially equivalent structures may be used for conveying a gas to and/or from the respiratory tract of an individual. Thus, it is considered that it will be a matter of routine to substitute for the outlet 56 a conventional mouthpiece (not shown) as used in many scuba type apparatuses. Similarly, in extreme circumstances the end 54 of the tube 52 could be especially shaped so as to be adapted to be inserted directly into the trachea of a patient.

The utilization of the apparatus 10 is essentially a rather simple matter. Preferably prior to the outlets 56 being inserted into the nostrils of a user the valve 42 is actuated so as to supply a gas—normally oxygen in the preferred utilization of the invention in administering oxygen to a patient—to the device 12. As this is done the sack 46 will normally be in a collapsed or empty configuration. The gas supplied will tend to purge the apparatus 10 to a large extent and will also to a limited degree tend to inflate the sack 46 to a slight extent.

After the gas supplied has reached the end 54 the outlets 56 are preferably inserted within the nostrils of the user. The end 54 is then preferably secured in place against accidental or inadvertent dislodgement by a conventional expedient such as, for example, through the use of a small quantity of adhesive tape in such a manner that as the user breathes so as to exhale some of the exhaled gas will pass between the exteriors of the outlets 56 and the interiors of the nostrils to the ambient surroundings. With the apparatus 10 in place in this manner the individual will thereafter breathe in essentially a normal manner.

On exhalation a part of the breath of the individual will be vented to the ambient atmosphere and the remainder will create what may be regarded as a back pressure in the tube 52. This change in the flow through the tube 52 will cause a change in the flow through the respiration chamber 26. This change will then be manifested through the first feedback passage 34 at the supply port 20. The flow through the passage 34 will act on the stream of compressed gas being emitted from the supply port 20 so as to tend to direct this gas toward the output port 28. Concurrently some of the gas flow from the tube 52 generally away from the end 54 will also flow through the chamber 26 and the port 24 into the output port 28. As a consequence of this type of action gas will be conveyed through the reservoir chamber 30 to the sack 46 so as to cause this sack 46 to increase in volume or inflate until such time as the patient inhales.

During such inhalation the pressure within the tube 52 will be altered in such a manner that gas can flow from the respiration chamber 26 of the device 12 to the user. As there is such a reversal of pressure the pressure in the respiration chamber 26 will be reduced. This will cause a corresponding drop in the pressure in the first feedback passage 34. As a consequence of both of these factors the flow from the supply port 24 will be directed toward the respiration chamber 26. Such flow will exercise a Venturi effect tending to exhaust the sack 46 through the chamber 30 and the port 28 and around the splitter 32 and to a lesser extent through the feedback passage 36. As a consequence of this the user will inhale through the tube 52 a mixture of the gas formerly within the sack 46 and a mixture of the gas from the tank 38 during inhalation. On subsequent exhalation from the respiratory tract a part of the exhaled gas will again be vented to the atmosphere through the nostrils around the outlets 56 while a part of the exhaled gas will be used to create a back pressure starting the sequence indicated in the preceding over again.

It will be realized from the aforegoing that during exhalation a gas mixture will be supplied to a tube 52 from the respiratory tract of the user. Depending upon the length of this tube 52 such a mixture may even be supplied to the device 12 and to the sack 46. It will also be realized that on inhalation such previously exhaled gas will be inhaled. As a result of this on some occasions the amount of carbon dioxide inhaled by an individual may be higher than desired because of the fact that carbon dioxide is released by the body on exhalation.

It is not considered that this will normally be a problem in connection with the apparatus 10 because of the fact that a significant part of the exhaled gas mixture will be vented directly to the ambient atmosphere. If, however, this carbon dioxide buildup within the apparatus 10 is regarded as a problem it is possible to incorporate within the tube 52 a conventional cannister 58 of a material which will react with carbon dioxide so as to remove it from a gas stream. The use of such a cannister 58 is regarded as particularly desirable in an apparatus corresponding to the apparatus 10 used for scuba purposes.

On occasion, as, for example, when the breath of a user is apt to contain entrained material it may be desirable to utilize a further conventional cannister 60 within the tube 52 containing a conventional filter and/or a water absorbent such as silica gel. As a precautionary measure a similar cannister 62 containing a filter and/or a water absorbent may be inserted in the line 40. These cannisters 60 and 62 are considered desirable when there is any reasonable chance of moisture and/or entrained more solid material being conveyed into the interior of the device 12. If moisture should condense within the interior of this device 12 or if various contaminants should become lodged within it there is a significant chance that the operation of the device 12 will be detrimentally affected.

The use of a fluidic device 12 in the complete apparatus 10 is advantageous because of the comparative low cost and simplicity of this device 12. Because of its simplicity the device 12 is capable of being rendered inoperative in its intended mode by contaminants such as are indicated in the preceding. However, because of its simplicity the device 12 eliminates various electrical and/or mechanical type problems as are inherent in prior art "rebreather" type breathing apparatuses. The complete apparatus 10 is, because of the use of the device 12, quite desirable in that it tends to minimize any waste of oxygen during oxygen therapy. This is considered important in making such therapy available at an affordable cost to many patients.

I claim:

1. In a breathing apparatus having a supply means for supplying a gas capable of being breathed, an enclosed reservoir means for temporarily storing a gas, a respiration means for conveying a gas to and from the respiratory tract of an individual and a control means responsive to the inhalation and exhalation from and into said respiration means, said control means being connected to said supply, reservoir and respiration means, in which the improvement comprises:
    said fluidic control device comprises a bistable fluidic amplifier having a first input port directly connected to said source, a second port directly connected to said reservoir means and a third port directly connected to said respiration means, said fluidic control device containing no moving parts and including means responsive only to a variation in the gas pressure within said respiration means so as to permit flow from both said supply means and said reservoir means into said respiration means upon inhalation through said respiration means and so as to cause gas flow from said supply means into said reservoir means upon exhalation into said respiration means.

2. A breathing apparatus as claimed in claim 1 wherein:
    said fluidic means comprises a housing including a supply chamber, an output respiratory chamber, an output reservoir chamber, an interaction chamber, a supply port leading to said supply chamber into said interaction chamber, an output port leading from said interaction chamber to said respiration chamber, an output port leading from said interaction chamber to said reservoir chamber, a splitter located between said output ports, said outputs ports and said splitter being located on the opposite side of said interaction chamber from said supply port generally in line with said supply port, said splitter being located so as to split the flow from said interaction chamber into the output to the respiration chamber or the output to the reservoir chamber,
    said output reservoir chamber being connected to said reservoir means, said output respiration chamber being connected to said reservoir means.

3. A breathing apparatus as claimed in claim 2 wherein:
    said fluidic means also includes a first feedback passage leading from said respiration chamber to said interaction chamber adjacent to said supply port and a second feedback passage leading from said reservoir chamber to said interaction chamber adjacent to said supply port, said feedback passages intersecting said interaction chamber on opposite sides of said supply port at locations such that the flow from the supply port is directed to either said respiration chamber or said reservoir chamber.

4. A breathing apparatus as claimed in claim 1 wherein:
    said supply means is a source of compressed oxygen.

5. A breathing apparatus as claimed in claim 1 wherein:
    said reservoir means is an accumulator means capable of varying in internal volume in accordance with the quantity of said gas within said accumulator means.

6. A breathing apparatus as claimed in claim 1 wherein:
    said reservoir means comprises a flexible, elastomeric sack.

7. A breathing apparatus as claimed in claim 1 wherein:
    said respiration means comprises tube means, an extremity of which is adapted to be inserted within a body opening connected to the respiratory tract of a user.

8. A breathing apparatus as claimed in claim 7 wherein:
    said extremity of said tube means fits within said body opening so that on exhalation some exhaled gas will be vented to the ambient atmosphere while other exhaled gas will apply a back pressure to said control means through said respiration means.

9. A breathing apparatus as claimed in claim 1 wherein:
    said respiration means comprises a tube having an end remote from said control means provided with two tubular outlets adapted to fit loosely within the nostrils of a user.

10. A breathing apparatus as claimed in claim 1 wherein:
    said fluidic means comprises a housing including a supply chamber, an output respiratory chamber, an output reservoir chamber, an interaction chamber, a supply port leading to said supply chamber into said interaction chamber, an output port leading from said interaction chamber to said respiration chamber, an output port leading from said interaction chamber to said reservoir chamber, a splitter located between said output ports, said output ports and said splitter being located on the opposite side of said interaction chamber from said supply port generally in line with said supply port, said splitter being located so as to split the flow from said interaction chamber into the output to the respiration chamber or the output to the reservoir chamber, said output reservoir chamber being connected to said reservoir means, said output respiration chamber being connected to said respiration means, said fluidic means also includes a first feedback passage leading from said respiration chamber to said interaction chamber adjacent to said supply port and a second feedback passage leading from said reservoir chamber to said interaction chamber adjacent to said supply port, said feedback passages intersecting said interaction chamber on opposite sides of said supply port at locations such that the flow from the supply port is directed to either of the respective supply ports, said reservoir means comprises a flexible, elastomeric sack.

11. A breathing apparatus as claimed in claim 10 wherein:

said respiration means comprises a tube having an end remote from said control means provided with two tubular outlets adapted to fit loosely within the nostrils of a user, said supply means is a source of compressed oxygen.

12. A breathing apparatus as claimed in claim 11 wherein:

said respiration means includes nasal cannula means capable of fitting loosely within the nostrils of said individual so that on exhalation some exhaled gas will pass to the ambient around the exterior of said nasal cannula means.

13. A breathing apparatus for use in supplying a gas capable of being breathed from a supply means to an individual which comprises:

a respiration means for conveying a gas to and from the respiratory tract of an individual while permitting some gas exhaled by said individual to pass to the ambient surroundings, a reservoir means for temporarily storing only gas received from said supply means, and a fluidic flip-flop logic control means containing no moving parts for controlling flow of a gas from said supply means and for controlling flow into and out of said reservoir means and for conveying gas into and from said respiration means solely in response to fluid pressure in said respiration means, said fluidic control means having an inlet connected to said supply means, a port connected to said reservoir means, and another port connected to said respiration means, said fluidic means being responsive to variations in gas pressure generated by a change in the breathing of said individual to permit flow from both said supply means and said reservoir means to said individual upon inhalation by said individual and to cause flow from said supply means to said reservoir means upon exhalation of said individual.

* * * * *

UNITED STATES PATENT AND TRADEMARK OFFICE
CERTIFICATE OF CORRECTION

PATENT NO. : 4,120,300
DATED : OCTOBER 17, 1978
INVENTOR(S) : BRIAN L. TIEP

It is certified that error appears in the above-identified patent and that said Letters Patent are hereby corrected as shown below:

Column 5, line 49, add the following phrase at the beginning of the body of claim 1:

--said control means being a fluidic control device,--

Signed and Sealed this

Tenth Day of June 1980

[SEAL]

Attest:

SIDNEY A. DIAMOND

Attesting Officer

Commissioner of Patents and Trademarks